(12) United States Patent
Warhurst et al.

(10) Patent No.: US 8,367,022 B2
(45) Date of Patent: Feb. 5, 2013

(54) UNINTENDED MOTION CONTROL FOR MANUALLY DIRECTED MULTI-CHANNEL ELECTRONIC PIPETTOR

(75) Inventors: Julian Warhurst, Ashland, MA (US); Richard Cote, Bolton, MA (US)

(73) Assignee: Integra Biosciences Corp., Hudson, NH (US)

( * ) Notice: Subject to any disclaimer, the term of this patent is extended or adjusted under 35 U.S.C. 154(b) by 0 days.

(21) Appl. No.: 13/099,953

(22) Filed: May 3, 2011

(65) Prior Publication Data

US 2011/0268628 A1  Nov. 3, 2011

Related U.S. Application Data

(60) Provisional application No. 61/330,545, filed on May 3, 2010.

(51) Int. Cl.
  *B01L 3/02* (2006.01)
(52) U.S. Cl. ........ 422/509; 422/511; 422/516; 422/522; 422/524; 422/525; 73/863.32; 73/864; 73/864.01; 73/864.11; 73/864.24; 73/864.25
(58) Field of Classification Search .................. 422/509, 422/511, 516, 519–522, 524–525, 63–68.1; 73/863.32, 864, 864.01, 864.11, 864.13, 73/864.16–864.21, 864.25, 864.31
See application file for complete search history.

(56) References Cited

U.S. PATENT DOCUMENTS

| | | | |
|---|---|---|---|
| 4,478,094 A * | 10/1984 | Salomaa et al. | 73/863.32 |
| 4,555,957 A * | 12/1985 | Frankel et al. | 73/864.14 |
| 5,116,180 A | 5/1992 | Fung et al. | |
| 5,895,630 A * | 4/1999 | Skaborn et al. | 422/509 |
| 6,270,726 B1 * | 8/2001 | Tyberg et al. | 422/509 |
| 6,360,792 B1 | 3/2002 | Ganz et al. | |
| 6,627,446 B1 * | 9/2003 | Roach et al. | 436/43 |
| 6,637,473 B2 * | 10/2003 | Ganz et al. | 141/130 |
| 6,982,063 B2 | 1/2006 | Hamel et al. | |
| 7,105,132 B2 * | 9/2006 | Shumate et al. | 422/510 |
| 7,135,146 B2 * | 11/2006 | Johnson et al. | 422/521 |
| 7,540,205 B2 | 6/2009 | Nelson et al. | |
| 7,662,343 B2 | 2/2010 | Mathus et al. | |
| 7,662,344 B2 | 2/2010 | Mathus et al. | |
| 8,033,188 B2 | 10/2011 | Kalmakis et al. | |
| 2001/0005489 A1 * | 6/2001 | Roach et al. | 422/99 |

(Continued)

FOREIGN PATENT DOCUMENTS

WO  2009/130318  10/2009

OTHER PUBLICATIONS

Rainin Pipetting 360°Simultaneous 96-well pipetting, Fast manual benchtop system, 2009 Rainin Instrument, LLC, PB-210 LIQ RevB, 2 pages.

(Continued)

*Primary Examiner* — Brian R Gordon
(74) *Attorney, Agent, or Firm* — Andrus, Sceales, Starke & Sawall, LLP

(57) ABSTRACT

A manually directed, electronic multi-channel pipettor uses servo controlled motors to drive a carriage and pipetting head in response to a user's manipulation of a control handle. The pipetting head include an array of tip fittings, e.g. 96. The system includes a check processor to avoid unintended motion in case of system faults or crashes. The system requires substantial force to attach the array of tips, and therefore includes controls that require both of the user's hands be occupied during the tip attachment process.

8 Claims, 13 Drawing Sheets

U.S. PATENT DOCUMENTS

| | | | |
|---|---|---|---|
| 2001/0048899 A1* | 12/2001 | Marouiss et al. | 422/100 |
| 2005/0249635 A1 | 11/2005 | Okun et al. | |
| 2006/0048846 A1 | 3/2006 | Roenneburg | |
| 2007/0221684 A1 | 9/2007 | Steinbrenner et al. | |
| 2009/0074622 A1 | 3/2009 | Kalamakis et al. | |
| 2009/0226344 A1* | 9/2009 | Nishida et al. | 422/67 |
| 2009/0274587 A1 | 11/2009 | Butz et al. | |
| 2011/0039709 A1* | 2/2011 | Lips et al. | 506/7 |
| 2011/0209564 A1* | 9/2011 | Von Beichmann et al. | 73/864.01 |
| 2011/0268627 A1 | 11/2011 | Warhurst et al. | |
| 2011/0296931 A1 | 12/2011 | Warhurst | |

OTHER PUBLICATIONS

Rainin Pipetting 360° Liquidator 96, Manual benchtop pipetting system, 2008 Rainin Instrument, LLC, 9920-360 Rev. B, 16 pgs.

CyBi-Well Pipettor User Manual, Release Sep. 2008, 88 pgs.

Thermo Scientific Matrix Hydra II, Product Specification, 2008 Thermo Fisher Scientific, Inc., 2 pgs.

Thermo Scientific Matrix PlateMate 2×3, Product Specification, 2007 Thermo Fisher Scientific, Inc., 2 pgs.

Thermo Scientific Matrix PlateMate Plus, Product Specification, 2007 Thermo Fisher Scientific, Inc., 2 pgs.

* cited by examiner

UNINTENDED MOTION CONTROL FOR MANUALLY DIRECTED MULTI-CHANNEL ELECTRONIC PIPETTOR

FIELD OF THE INVENTION

The invention relates to a manually-directed, electronic pipetting system having a multi-channel pipetting head with a plurality of pipetting channels, e.g., 96-channels, arranged in an array of rows and columns. In particular, the invention pertains to protecting against unintended motion, e.g. when attaching disposable pipette tips onto fittings of the pipetting head or otherwise.

BACKGROUND OF THE INVENTION

Multi well-plates, also known as microtiter plates or micro well-plates, are standard products in clinical and research laboratories. A multi-well plate is a flat plate with multiple wells used as individual test tubes. The most common multi-well plates include 96-wells or 384-wells arranged in a rectangular matrix. ANSI has set standardized dimensions and SBS footprints for well-plates. For example, a 96-well plate has 8 rows and 12 columns of wells centered 9 mm centerline-to-centerline. A typical 384-well plate includes 16 rows and 24 columns of wells with a centerline-to-centerline distance of 4.5 mm. Multi well-plates with 1536 wells and higher are also available. Some multi well-plates are designed to hold larger volumes than the standard multi well-plate, yet maintain the standard centerline-to-centerline dimensions. These well-plates are taller and are commonly called deep well-plates.

In a laboratory, multi well-plates are filled with various liquid samples, and it is routine to transfer liquid samples from one wellplate to another in order to implement assays or store duplicate samples. It is also routine to transfer liquid reagents or samples from a common reservoir to either a standard multi-well plate or a deep well-plate. Often, hand-held, multi-channel pipettors, with 8, 12 or 16 disposable pipette tips mounted thereto, are used to draw some or all of the liquid from a set of wells in one wellplate and transfer aliquots into another set of wells in the same wellplate or another wellplate. Pipettors and pipette tips come in various sizes in order to accommodate different volumes of liquid transfer. In order to produce a high volume of prepared multi well-plates, automated liquid handling machines have been developed to provide much higher throughput than a technician, even one using a multi-channel pipettor. In the art, there are several types of automated liquid handling machines to automatically fill multi well-plates. Such automated liquid handling machines typically use sophisticated Cartesian robots for positioning the disposable pipette tips, while shuttling well-plates from storage and into position for liquid transfer. It is common for these automated liquid handling machines to use removable and replaceable pipetting heads in order to accommodate various sized pipette tips.

Most of these automated liquid handling machines are rather expensive, and also quite large. Many include sophisticated computer control which requires extensive training, as well as set up and programming. Such automated, high-throughput systems are not practical for some applications. In order to address this need, the prior art includes, e.g., a simultaneous 96-well manual pipetting system. This fully manual system includes an array of pipette tip fittings matching the dimensions of a standard 96 well-plate, and aspirates and dispenses liquid from 96-disposable pipette tips simultaneously. The pipette tips are mounted to the 96-tip fittings using a levered mechanical mechanism. Because the system is fully manual, it lacks the ability to program precise protocols and liquid transfer amounts. On the other hand, electronic hand-held pipettors and automated liquid handling systems can be programmed to aspirate a precise volume of liquid reagent or sample and then dispense the aspirated volume, sometimes as a series of equal volume aliquots in successive dispensing operations. Programmable electronic hand-held pipettors and automated liquid handling systems can also be configured to do quite complex pipetting operations, such as mixing, repeat pipetting, diluting, etc.

While programmable, automated liquid handling systems have many desirable features over a fully manual 96-well liquid transfer system, they are generally too large and expensive for certain laboratory applications. To address this issue, the Assignee of the present application has developed a manually directed, electronic multi-channel pipetting system having a pipetting head with a plurality of pipetting channels arranged in a two-dimensional array of rows and columns, preferably 96-channels arranged in an array of 8 rows and 12 columns correlating to a standard 96 well-plate. The system is described in Assignee's co-pending patent application entitled "Manually-Directed, Electronic Multi-Channel Pipetting System", application Ser. No. 13/099,782,by Julian Warhurst, Gary Nelson and Richard Cote, filed on even date herewith, Publication No. U.S. 2011/0268627 A1, published Nov. 3, 2011, and incorporated herein by reference. In the Assignee's manually-directed, electronic 96-channel pipetting system, the pipetting head is mounted to a movable carriage that is attached to a tower containing a drive system for the pipetting head. A deck with at least one, but preferably two or more, wellplate nesting receptacles is located in front of the tower and is accessible by the pipetting head. The tower contains a drive system to raise and lower the pipetting head to aspirate and dispense reagents or samples in the well-plates or reservoirs placed in the nesting receptacles.

The Assignee's system also includes a control handle and a menu-driven software programming interface that is the same or quite similar to the control handle and programming interface on hand-held electronic pipettors sold by the Assignee, see e.g., the disclosures in U.S. Pat. No. 7,540,205 entitled "Electronic Pipettor", issuing on Jun. 6, 2009, based on U.S. patent application Ser. No. 11/856,231 by Gary E. Nelson, George P. Kalmakis, Kenneth Steiner, Joel Novac, Jonathan Finger, and Rich Cote, filed on Sep. 17, 2007, and incorporated herein by reference; and "Pipettor Software Interface", application Ser. No. 11/856,232 by George P. Kalmakis, Gary Nelson, Gregory Mathus, Terrence Kelly, Joel Novak, Kenneth Steiner and Jonathan Finger, filed Sep. 17, 2007, assigned to the Assignee of the present application and incorporated herein by reference, now U.S. Pat. No. 8,033,188 B2, issued Oct. 11, 2011. One of the benefits of the similarity is that users comfortable with the Assignee's hand-held pipettors are able to easily crossover to use the Assignee's manually assisted, electronic 96-channel pipetting system. In the Assignee's 96-channel system, however, the control handle is mounted to a load cell attached to the carriage for the pipetting head. The load cell detects force exerted on the control handle and outputs a corresponding signal to an electronic motor control system. In use, the user grabs the control handle in a manner similar as to when using a hand-held electronic pipettor, and exerts pressure on the control handle so that the electronic motor control system moves the pipetting head relative to the well-plates and reservoirs on the deck. In the preferred embodiment, the tower contains a motorized, z-axis drive mechanism for vertically raising and lowering the pipetting head with respect to the wellplate deck, and a motorized x-axis drive mechanism for moving the tower and pipetting head laterally, both being driven in response to sensed force exerted on the control handle. If the user presses on the control handle from left to right, the tower along with the pipetting head moves from left to right. If the user pulls the control handle upward, or pushes downward on the control handle, the z-axis drive mechanism raises or lowers the pipetting head accordingly.

While Assignee's manually directed, electronic 96-channel pipetting system preferably incorporates the user interface and menu-driven software similar to Assignee's single-channel and multi-channel, hand-held pipettors, other aspects of a 96-channel pipetting system must be handled quite differently.

SUMMARY OF THE INVENTION

When attaching an array of 96-pipette tips simultaneously to tip fittings on a pipetting head, the required cumulative insertion force is significantly greater than with a single channel, hand-held pipettor or an 8-, 12- or 16-channel hand-held pipettor. In accordance with the invention, the motorized, vertical drive mechanism used to raise and lower the pipetting head is used to generate enough force for simultaneous insertion of 96-tip fittings into 96-disposable pipette tips. However, such force is not necessary and not desirable under normal operating conditions other than for tip attachment. In one aspect of the invention, the system includes a detector (e.g. a force detector) for the vertical drive mechanism that generates a safety signal that is transmitted to the electronic control system if the vertical drive mechanism meets unexpected resistance. If triggered, the system stops the motor for the vertical drive mechanism from further downward movement. If a tip attachment sequence needs to be initiated, the safety trigger is overridden.

Another aspect of the invention recognizes the desirability of keeping the user's hands free of the motor driven pipetting head during the tip attachment process in order to protect the user from injury. In this regard, the preferred embodiment of the invention is implemented in a system having a multi-channel pipetting head with 96-tip fittings. The multi-channel pipetting head is preferably carried in a carriage mounted to a tower. A deck is located below the pipetting head and is adapted to hold at least one multi-wellplate or reagent reservoir, as well as a tip tray full of an array of 96-pipette tips. A control handle, preferably mounted to the carriage for the pipetting head, is held in the hand that the user normally uses for pipetting. An electronic control system that moves the pipetting head relative to the deck in accordance with the direction and amount of force applied to the control handle, as described in accordance with the above mentioned co-pending patent applications. In accordance with this aspect of the present invention, the system includes a tip attach button that must be activated in order to continue lowering the pipetting head to attach the disposable pipette tips to the tip fittings on the pipetting head. As mentioned, the required tip insertion force may be significant. The tip attach button is preferably located on the top of the carriage for the pipetting head, and requires activation by the user's other hand. In this manner, the user's hands are occupied when the vertical drive mechanism lowers the pipetting head to insert the tip fittings into the pipette tip collar, thereby preventing the opportunity that one of the user's hands be located in an unsafe location when the tips are being attached. In accordance with the invention, it is not necessary for the tip attach button to be located on the top of the carriage. The tip attach button may be located on another part of the system, or may be located on the laboratory bench top.

The preferred method of attaching the disposable pipette tips involves the following steps. First, a tip rack full of disposable tips is placed on one of the wellplate nesting receptacles on the deck. Then, using the control handle, the pipetting head is lowered and aligned over the tip rack. Most preferably, the electronic control system biases the pipetting head into proper vertical alignment prior to allowing the pipetting head to descend downward to insert the tip fittings into the respective pipette tips. The preferred manner of biasing is described in co-pending patent application entitled "Pipetting Tip Positioning for a Manually-Directed, Electronic Multi-Channel Pipetting System", based on U.S. Provisional Application No. 61/330,551, filed on even date herewith, now U.S. patent application Ser. No. 13/099,854, filed May 3, 2011, Publication No. U.S. 2011/0296931 A1, published Dec. 8, 2011, by Julian Warhurst, assigned to the Assignee of the present invention and incorporated herein by reference. Once the pipetting head is aligned with the tip fittings hovering over the respective pipette tips, the user pushes down on the control handle to lower the tip fittings into the pipette tip collars. The increased force load on the pipetting head should trip the safety switch to stop further downward movement. The software checks that the tip fittings are located in the proper location, height and lateral position for the pipette tips of interest and then provides a signal to the user, such as illuminating a tip attach button on the top of the carriage for the pipetting head. At this point, the operation of the servo control system is disabled and the tip attachment cycle is ready for initiation. To do this, the user will depress the tip attach button with one hand and press downward on the control handle with the other hand. The pipetting head is lowered a fixed distance and held momentarily to ensure attachment of the pipette tips. Then the pipetting head is automatically lifted up to clear the tips from the tip box. At that time, normal servo control is returned to the user.

Preferably, the tip fittings and the pipette tips are the same or similar to that described in U.S. Pat. Nos. 7,662,343 and 7,662,344 both entitled "Locking Pipette Tip and Mounting Shaft" by Greg Mathus, Terrence Kelly and Rich Cote, both assigned to the Assignee of the present application and incorporated herein by reference. The tip fittings described in these patents provide substantial lateral stability for the attached pipette tips. This enables the user to simultaneously touch off the mounted pipette tips, e.g. 96-pipette tips, and remain confident that the tips will remain properly attached and aligned on the tip fittings.

Another aspect of the invention pertains to the use of a check processor in the servo control system to prevent unintended motion of the pipetting head. More specifically, in accordance with the preferred embodiment of the invention, separate servo control loops are used to control the operation of the X-axis horizontal drive mechanism and Z-axis vertical drive mechanism respectively. Each servo control loop preferably includes a check processor which receives input signals from Hall-effect sensors associated with the respective motor. Under normal operating conditions, the check processor transmits to the motor driver an echo of the input signals from the Hall-effect sensors. In the event that the check processor detects a fault condition in the operation of the motor drive mechanism, the check processor will not transmit an echoed signal but rather supply a fault code to the motor driver. The motor will halt very shortly after it does not receive an appropriately echoed Hall-effect signal. In the preferred system, the halting of the motor in this manner is used to halt the motor in case: 1) a complete or partial failure of an encoder for one of the motors is detected, 2) a drive speed exceeding a maximum desired speed is detected, and 3) a failure of the vertical force detector described above with respect to the tip attachment procedure is detected.

Other features and advantages should be apparent to those skilled in the art upon reviewing the following drawings and description thereof.

DETAILED DESCRIPTION

Figure 1:
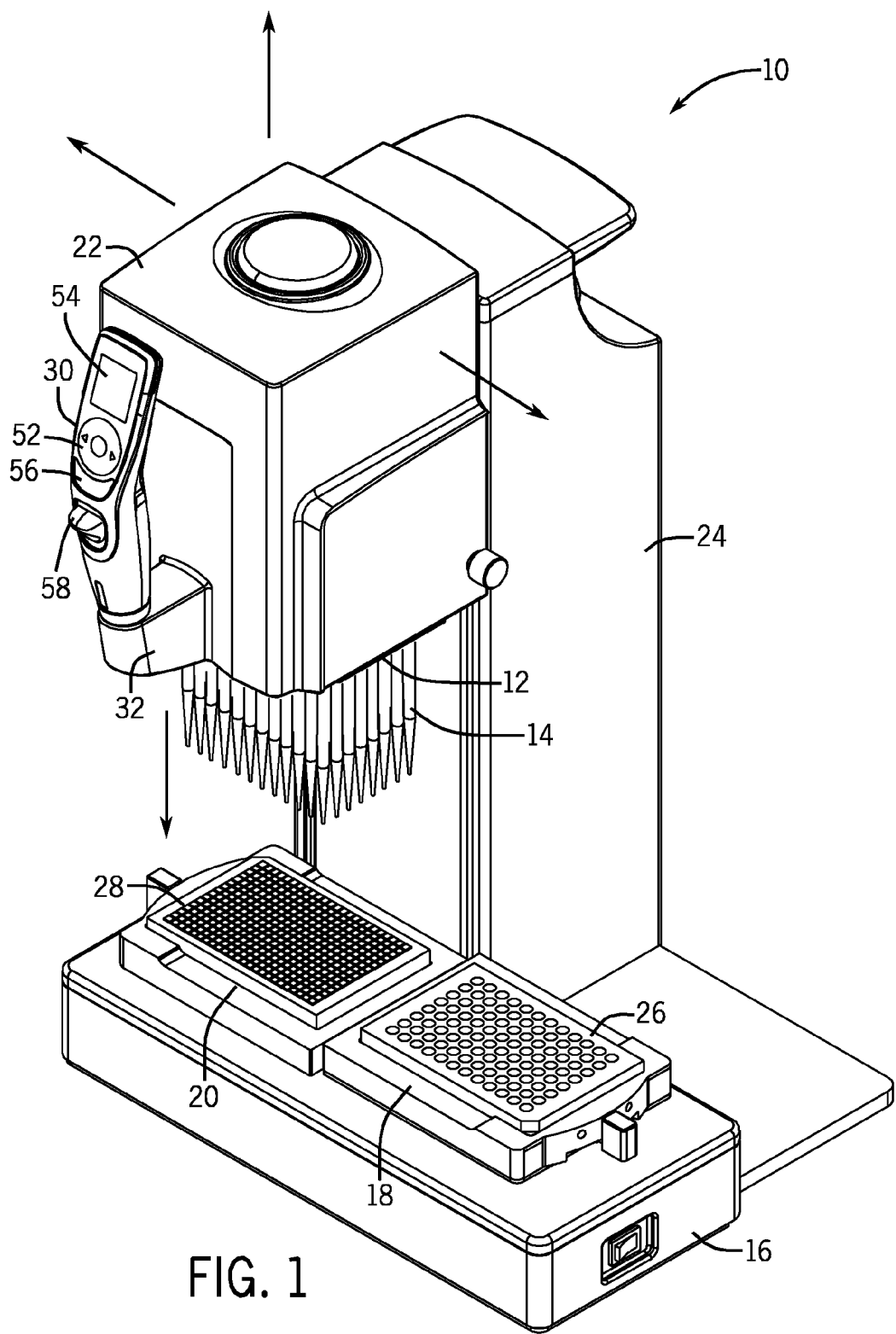
FIG. 1 is a perspective view an exemplary embodiment of a manually-directed, multi-channel pipetting system in which the invention may be used.
Figure 2:
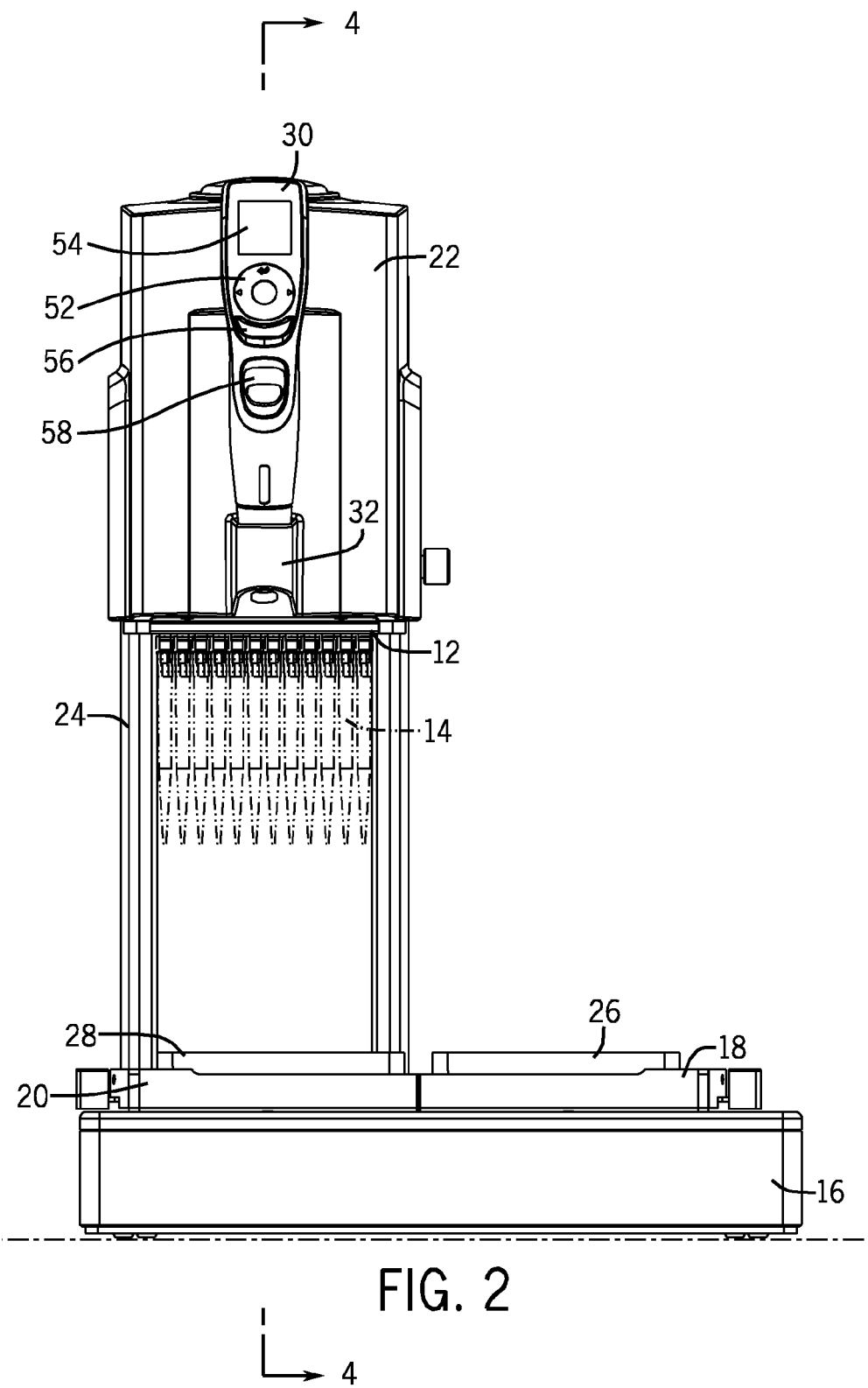
FIG. 2 is a front elevational view of the multi-channel pipetting system illustrated in FIG. 1.
Figure 3:
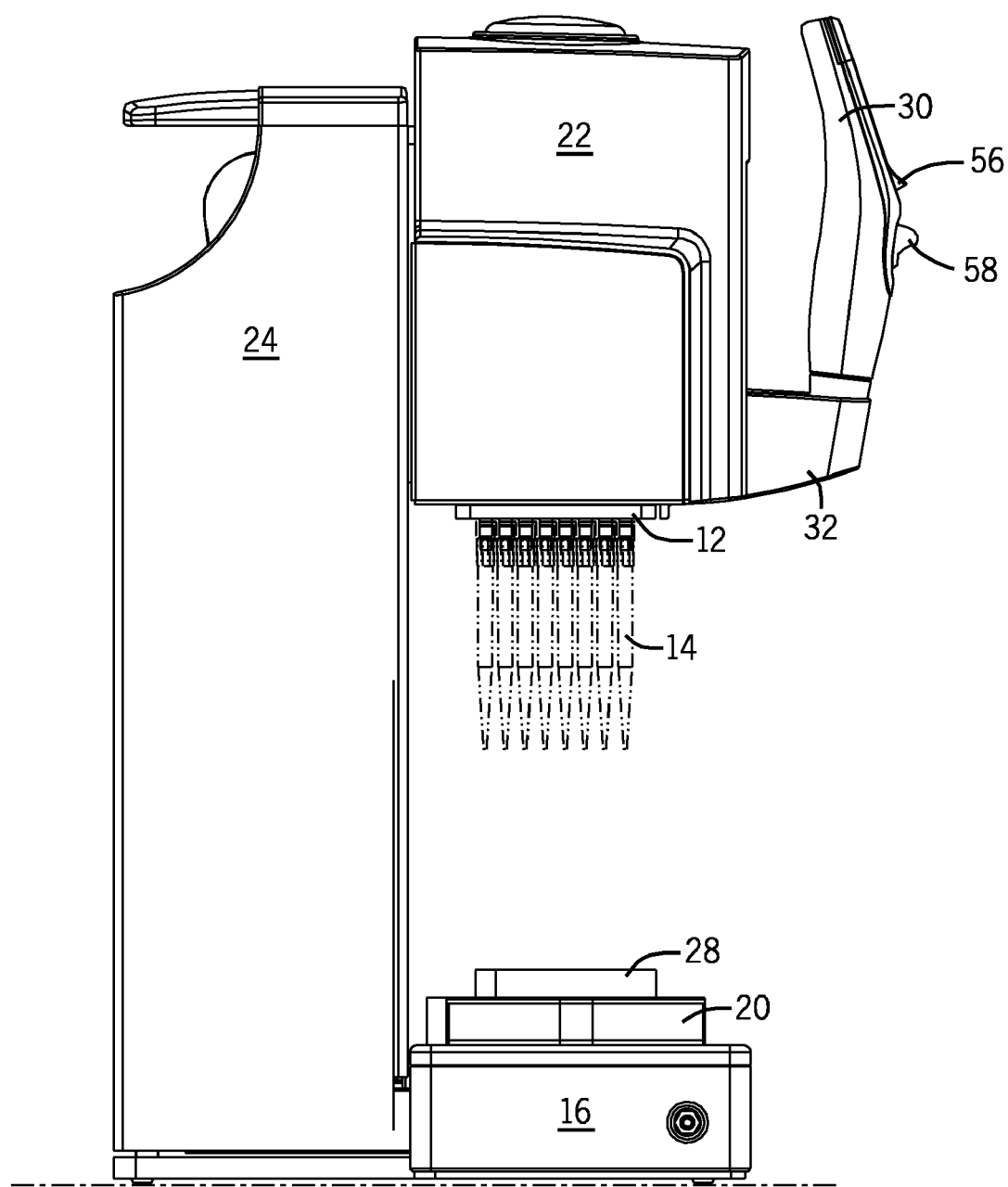
FIG. 3 is a side elevational view of the manually-directed, multi-channel electronic pipetting system illustrated in FIGS. 1 and 2.

An embodiment of a manually directed, multi-channel electronic pipetting system 10 as described in the above incorporated patent applications is shown in FIGS. 1-3. Referring to FIGS. 1-3, the manually directed, multi-channel electronic pipetting system 10 includes a multi-channel pipetting head 12 having a plurality of pipetting channels arranged in a two dimensional array of rows and columns. Normally, the pipetting head 12 will include an array of 96-tip fittings. An array of pipette tips 14 are attached to the multi-channel pipetting head 12. The manually directed, multi-channel electronic pipetting system 10 includes a flat deck 16 supporting a right nesting receptacle 18 and a left nesting receptacle 20. The nesting receptacles 18, 20 are designed to hold multi well-plates, reagent reservoirs or tip racks in a known location on the deck 16.

The pipetting head 12 is removably mounted to a carriage 22 which in turn is mounted to a tower 24. A pipetting motor located within the carriage 22 drives the multi-channel pipetting head 12 to aspirate and dispense. A Z-axis drive mechanism moves the carriage 22 and the multi-channel pipetting 12 vertically with respect to the tower 24 and the deck 16. An X-axis drive mechanism moves the tower 24 and the carriage 22 horizontally along an X-axis so that the pipetting head 12 and the array of tips 14 can be moved from a position corresponding to the wellplate 26 in the first nesting receptacle 18 on the deck 16 to positions corresponding to the wellplate 28 residing in the left side nesting receptacle 20.

The system 10 includes a control handle 30 preferably mounted to the carriage 22 and preferably resembling a handle for a handheld electronic pipettor. More specifically, the control handle 30 is preferably mounted to a load cell 32 that is attached to the carriage 22. In use, the user grasps the control handle 30 in the manner similar as when using a handheld pipettor, and exerts pressure on the control handle 30 to move the carriage 22 and the pipetting head 12. The vertical Z-axis motion and the horizontal X-axis motion are driven by independent motors under servo control. While it is preferred to use a load cell to sense the user's command of the control handle 30, other types of sensors such as potentiometers, optical sensors or laser sensors, etc., can be used within the spirit of the invention. The control handle 30 preferably includes a user interface for controlling pipetting functions such as aspirating and dispensing.

The use of the controller 30 as well as the overall operation of the system 10 is intended to replicate the natural hand motion of a user using a conventional handheld pipettor. However, with a conventional handheld pipettor, a user would not be able to reliably use a 96-channel pipetting head in part because it would be extremely difficult to properly align all 96-pipette tips with a detached handheld pipettor. The control handle 30 on the load cell 32 has two pairs of strain gauges, one for vertical force detection and one for horizontal force detection. The X-axis drive and the Z-axis drive operate independently and contemporaneously when a component of force input is measured by each respective pair of strain gauges. Software in the system controls motion of the pipetting head and smoothes operation, fosters precise alignment, and controls the assembly force exerted by the drive systems, etc.

Figure 4:
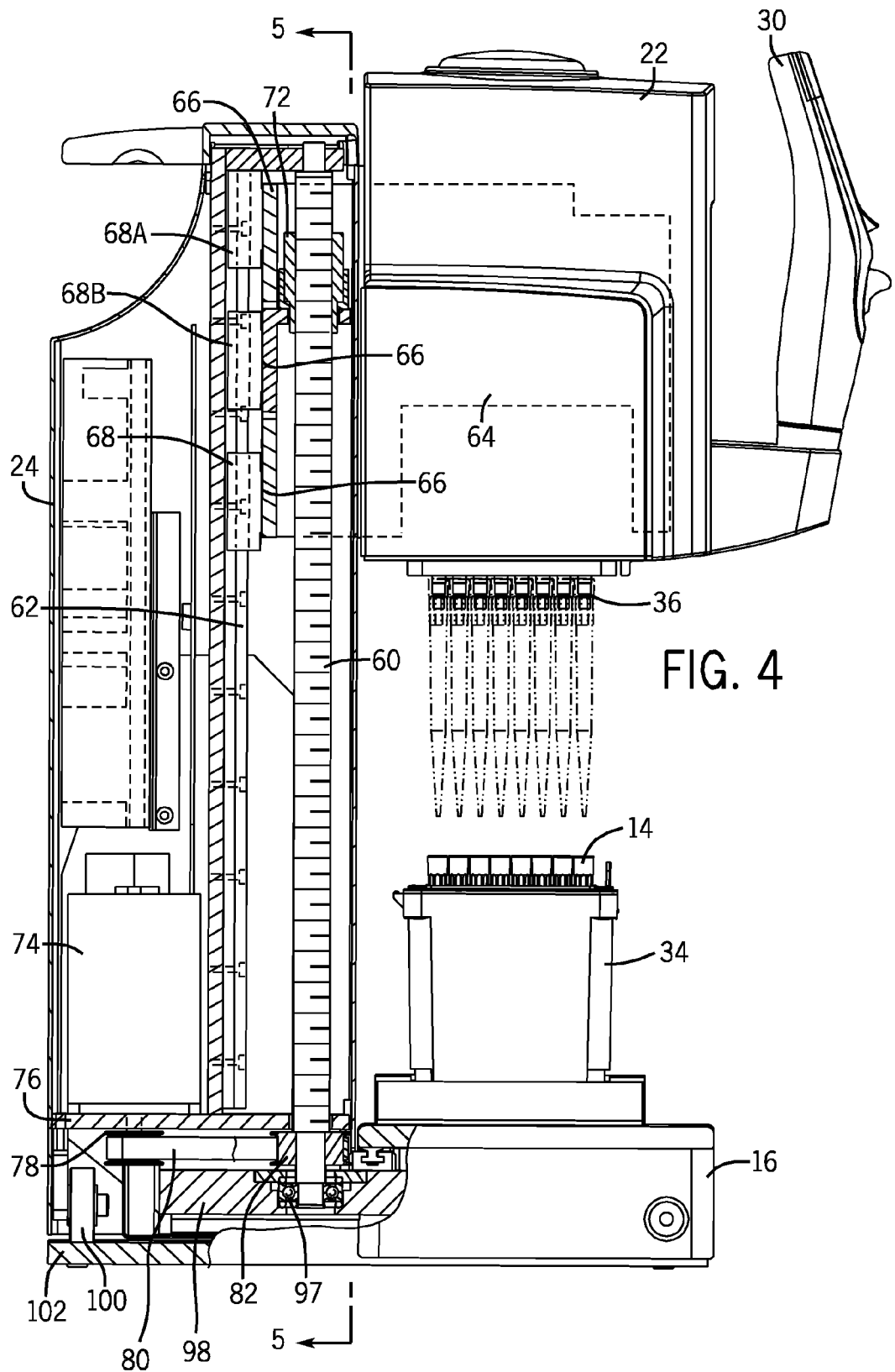
FIG. 4 is a side elevational view with parts broken away to illustrate components of the vertical drive mechanism, and also showing a tip container being placed within a nesting receptacle on the deck of the system.

The manually directed, multi-channel electronic pipetting system 10 must not only be capable of transferring fluids from and to selected locations, but must also provide for the practical and convenient attachment and ejection of the pipette tips. Referring to FIG. 4, the pipetting head 12 with the array of tip fittings 36 is aligned precisely over a tip container 34 located on deck 16 using the X-axis horizontal drive mechanism. Then, the Z-axis vertical drive mechanism is used to lower the carriage 22 and the tip fittings 36 with sufficient force to attach the array of pipette tips 14 held in the tip container 34. The carriage 22 and the pipetting head 12 are then raised using the Z-axis vertical drive mechanism to remove the tips 14 from the tip container 34. The tip container 34 is removed from the nested receptacle 20 on the deck 16, and replaced with a wellplate or reservoir in order to transfer fluids. For tip attachment as with regular motion control, the general horizontal and vertical motion of the carriage 22 and pipetting head 12 is controlled by the user by holding the controller 30 in their palm and applying pressure in the appropriate direction to position the pipetting head 12 over the tray of pipette tips 14. Precise alignment necessary for tip attachment would of course be quite difficult but for the use of biasing motion control software described in detail in co-pending patent application entitled "Pipette Tip Positioning for Manually-Directed Multi-Channel Pipettor", filed on even date herewith by Julian Warhurst, assigned to the Assignee of the present application and incorporated herein by reference. As discussed in more detail below, once the pipetting head 12 and the tip fittings 36 are aligned, the handle control 30 is disabled and an automated tip attachment routine is used to provide sufficient force to attach the tips 14 to the fittings 36.

Referring again to FIGS. 1-3, the preferred control handle 30 is the same or quite similar to that disclosed in issued U.S. Pat. No. 7,540,205 entitled "Electronic Pipettor" by Gary Nelson et al. issued on Jun 2, 2009, and incorporated herein by reference. The preferred control handle 30 not only provides a handle for attachment to the load cell 32 to control movement of the pipetting head, but also preferably provides a user input interface. The control handle 30 includes an elongated body adapted to be held in the hand of the user. A touch wheel control 52 is designed to be operated by the user's thumb. The touch wheel control 52 is located below a dot matrix user interface display 54. The preferred controller 30 also includes a run button 56 which is located below the touch wheel control 52 and an ejector button 58. In this exemplary embodiment, a printed circuit board with a dedicated microprocessor is located within the control handle 30, although the tower 24 contains a larger main printed circuit board containing several electronic components including an additional main microprocessor. The circular touchpad 52 translates rotational movement of the user's thumb (or finger) into cursor movements on the display 54 in order to navigate menu driven software. The menu driven software is, in many respects, similar to the software disclosed in co-pending application entitled "Pipettor Software Interface", application Ser. No. 11/856,232 by George Kalmakis et al., filed Sep. 17, 2007, now U.S. Pat No. 8,033,188 B2, issued Oct. 11, 2011, assigned to the assignee of the present application and incorporated herein by reference. As mentioned previously, the software provides graphic displays for adjusting volume, relative pipetting speed, pace and count for the various program pipetting procedures. The software also preferably provides multiple programmable pipetting modes based on predetermined algorithms, such as pipette, repeat pipette, sample dilute, pipette/mix, manual pipette, reverse pipette, variable dispense, variable aspirate, sample dilute/mix, and serial dilution. These functional modes are based upon predetermined algorithms embedded in the software to implement respective, well known pipetting procedures, although various parameters such as volume, speed, pace, count, direction and mixing are available for programming and editing for the user. In addition, the preferred software also includes a custom programming mode in which the user can create custom pipetting procedures based on the steps of aspirating, mixing, dispensing and purging. The preferred software also includes other features as well.

While the touch wheel control 52 and the display 54 are generally used to program the pipetting system, the display 54 is also used to show progress or status during an implemented pipetting routine. In this regard, the run button 56 is used to activate the system to aspirate or dispense, etc. in accordance with the pipetting protocol on the display 54. For example, consider a situation in which the pipette tips 14 are attached to the pipetting head 12 ready for use and a reagent reservoir is placed within nested receptacle 18 and a wellplate with samples is placed in nested receptacle 20, and it is desirable in accordance with a programmed protocol to transfer 20 µl of the reagent from the reservoir into each of the 96-wells in the well-plate. The user grasping the control handle 30 will first direct the carriage 22, pipetting head 12 and pipette tips 14 over the reservoir located in nesting receptacle 18. The display 54 may illustrate an instruction such as "aspirate 20 µ". The user will then lower the pipette tips 14 into the liquid in the reservoir by placing downward pressure on the control handle 30. Then, in order to aspirate 20 µl of the reagent into each pipette tip 14, the user will press run button 56 to activate the pipetting stepper motor to aspirate 20 ml of reagent into each pipette tip. The user will then lift the filled pipette tips 14 from the reagent reservoir in the first nesting receptacle 18 by pulling upward on the control handle 30. The next instruction on the display 54 may be "dispense 20 µl". The user will then move the filled pipette tips over the wellplate in the second nesting receptacle 20, and align the pipette tips over the appropriate wells in the wellplate by pressing against the control handle 30. The user will then lower the filled tips over the wells, and presses run button 56 to instruct the pipettor stepper motor to dispense the liquid in the pipette tips.

Figure 6:
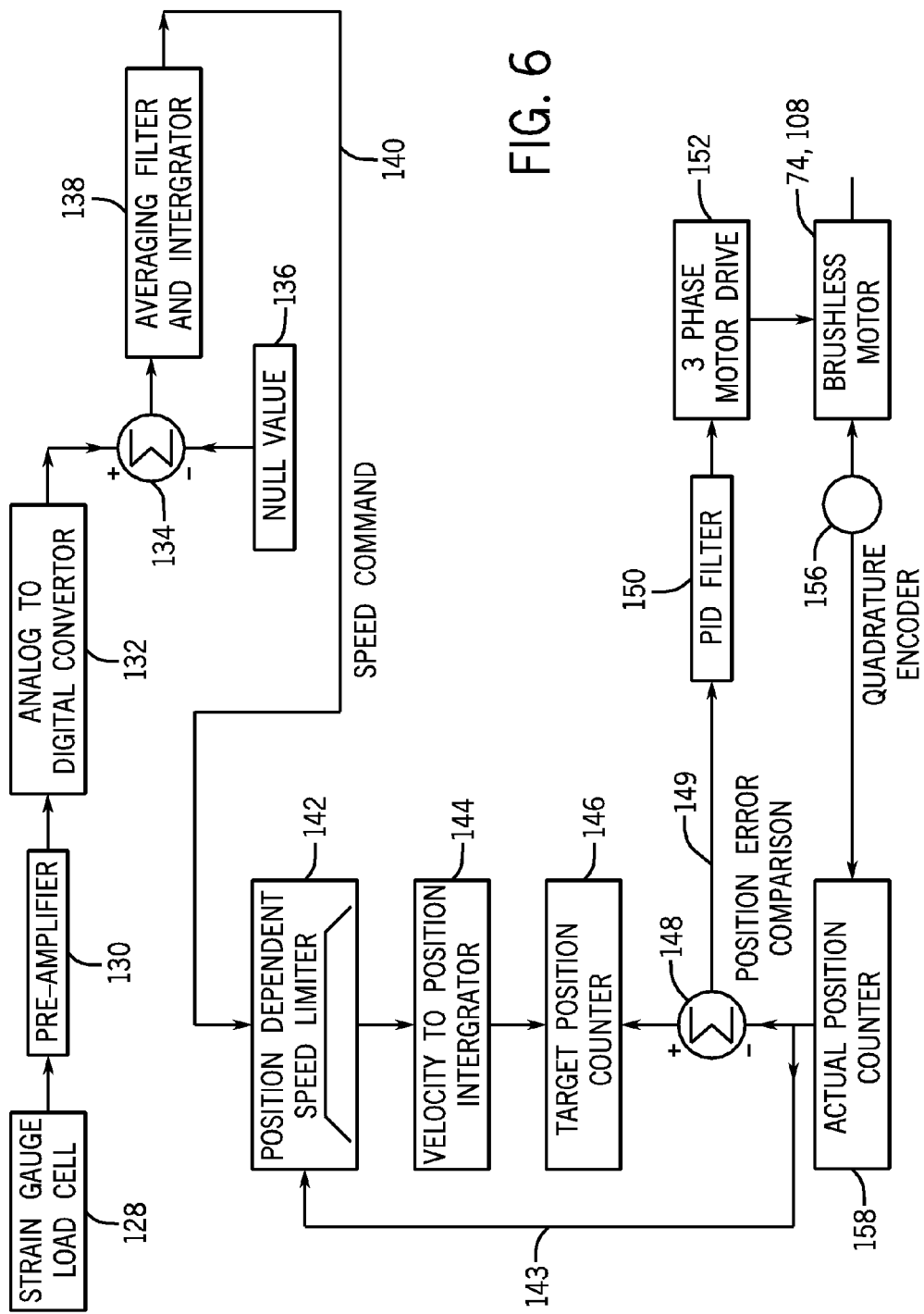
FIG. 6 is a block diagram illustrating an electromechanical and software control loop used in accordance with the preferred embodiment of the invention.

The general aspects of the motion control system, in free form mode (i.e. without the positioning bias feature), are described below in connection with FIG. 6. The servo motor 108 for horizontal movement and the servo motor 74 for vertical movement are preferably brushless 3-phase motors with encoders (156) operated with similar and independent control loops. Both vertical motion and horizontal motion can operate simultaneously depending on the force imparted on the control handle 30. FIG. 6 illustrates the general aspects of the preferred control loop in free form mode when the user imparts a force on the control handle 30. The detected horizontal component of the force as well as the detected vertical component force is characterized by the load cell as a signal that is initially amplified by a pre-amplifier 130 to a level suitable for A/D conversion. The voltage signal from the pre-amplifier 130 is converted into a digital force value preferably at a rate of 100 samples/second. The digital output signal form the A/D converter 132 is then null corrected, reference number 134. The null correction feature allows the load cell output to drift over time and/or have poor initial zero output. To determine the null value 136, the user is asked to remove their hand from the control handle 30, the A/D converter output 132 is then measured, and if stable that value it is stored as the null value 136. During normal operation, the null value is subtracted from the A/D converter output 132 and the output of the null subtraction 134 is in the range of +127 to −127 (2×108) with zero corresponding to no input from the user. The null correction feature is useful when the load cell 32 is overloaded due to misuse or accidental impact which may cause its "zero" value to change. Preferably, the null value will be reset whenever the system is re-initialized.

The null-corrected user force value is then passed through an averaging filter and integrator 138. The averaging filter and integrator 138 has two functions. First, since the load cell is subject to some vibration and noise during normal operation, the averaging filter 138 smoothes out the signal. Second, the integrator reduces the force that the user must impart by accumulating the force input over time. This provides the handheld controller 30 with a light feel and imparts a sensation of inertia which has been found to be desirable. The output from the averaging filter and integrator 138 is the requested speed value, line 140. The requested speed value is a speed limiting function, which is designated in FIG. 14 as block 142. The purpose of the speed limiting function 142 is to prevent crashing in the either vertical or horizontal direction at the end of the travel range. Crashing may cause damage, and also provides undesirable sensation. The requested speed value 140 is limited at the end of the mechanical travel range such that the speed is linearly reduced to zero as the end of the mechanical travel range is reached. To do this, the speed limiter 142 is updated with the actual position of the pipetting head from the encoder 156 and position counter 158 for the respective motor 74, 108. Line 143 illustrates the actual position data being fed back to the speed limiter 142. For the horizontal axis, the total travel is approximately 150 mm with the speed limiter coming into effect during the last 10 mm on either end of travel. For the vertical axis, the total travel is approximately 250. The position in which the speed limiter comes into effect preferably depends on the size and type of pipette tips being used.

The adjusted speed value from the speed limiter 142 is then integrated, e.g. at a rate of 1 kHz, to calculate a target position, see reference numbers 144 and 146. The target position is updated, e.g. 1,000 times/second, and represents the position that the respective servo motor 74, 108 should attempt to achieve, i.e. the classic target position for an industry standard PID controller.

The actual motor position is measured by accumulating the output of the digital encoder 156 attached to the respective servo motor 74, 108, see reference number 158. The actual position is then compared to the target position, see reference number 148, and the output is a position error value in line 149. The position error value in line 149 is passed through a proportional-integral-derivative filter 150, which calculates the desired motor output power. The desired motor output power signal is then fed to a 3-phase motor driver 152 which converts the signal to a pulse width modulation signal that is amplified through a 3-phase FET bridge and then fed to the servo motor 74, 108. The result of this control loop is that the motion of the pipettor head 12 tracks the hand motion imparted by the user on the control handle 30, with a natural feel and with end travel limits imposed in a gradual matter.

The mechanical aspects of the Z-axis vertical drive mechanism and the X-axis horizontal drive mechanism are described in detail in co-pending, incorporate patent application entitled "Manually Directed, Multi-Channel Electronic Pipetting System". While aspects of the present invention pertain to movement in the horizontal direction, certain aspects of the present invention are particularly directed to force detection along the Z-axis vertical drive mechanism. For this reason, the mechanical aspects of the Z-axis vertical drive mechanism are discussed herein with reference to FIGS. 4 and 5. The Z-axis vertical drive mechanism includes a vertically mounted lead screw 60 in the tower 24. The bottom of the lead screw 60 is mounted in a bearing 97 located on a horizontally movable support block 98. The horizontally movable support block 98 is moved by the X-axis horizontal drive mechanism. The horizontally movable support block 98 has one or more bearings mounted on rails for horizontal movement. FIG. 4 also shows a wheel 100 riding on bottom plate 102 to support the tower 24 for horizontal movement. In an alternative arrangement to that shown in FIG. 4, the horizontally movable support block 98 can be mounted on rails on the bottom plate 102 with bearings and without the wheel 100. A vertical guide rail 62 is also mounted vertically in the tower 24 and generally in parallel with the lead screw 60. A ball screw mechanism may be used as an alternative to a lead screw mechanism. Mounting plates 64 from the carriage 22 extend into the tower 24. Cross plates 66 span between the carriage mounting plates 64. Slidable support bushings 68 journaled to the vertical guide rail 62 are connected to the cross plates 66. The position of the guide rail 62 is stabilized by attachment to a support plate in the tower 24. A threaded follower 72 is seated on the lead screw 60. The follower 72 is attached to the cross plates 66, which in turn are attached to bushings 68A and 68B on the vertical rail 62. Servo motor 74 is mounted on base plate 76 in the tower 24. Servo motor 74 drives pulley 78, and in turn through belt drive 80 drives pulley 82, which is connected to lead screw 60. When the servo motor 74 is activated to turn lead screw 60, the follower 72 and hence the carriage 22 moves vertically up or down depending on the direction of rotation of the lead screw 60.

Figure 5:
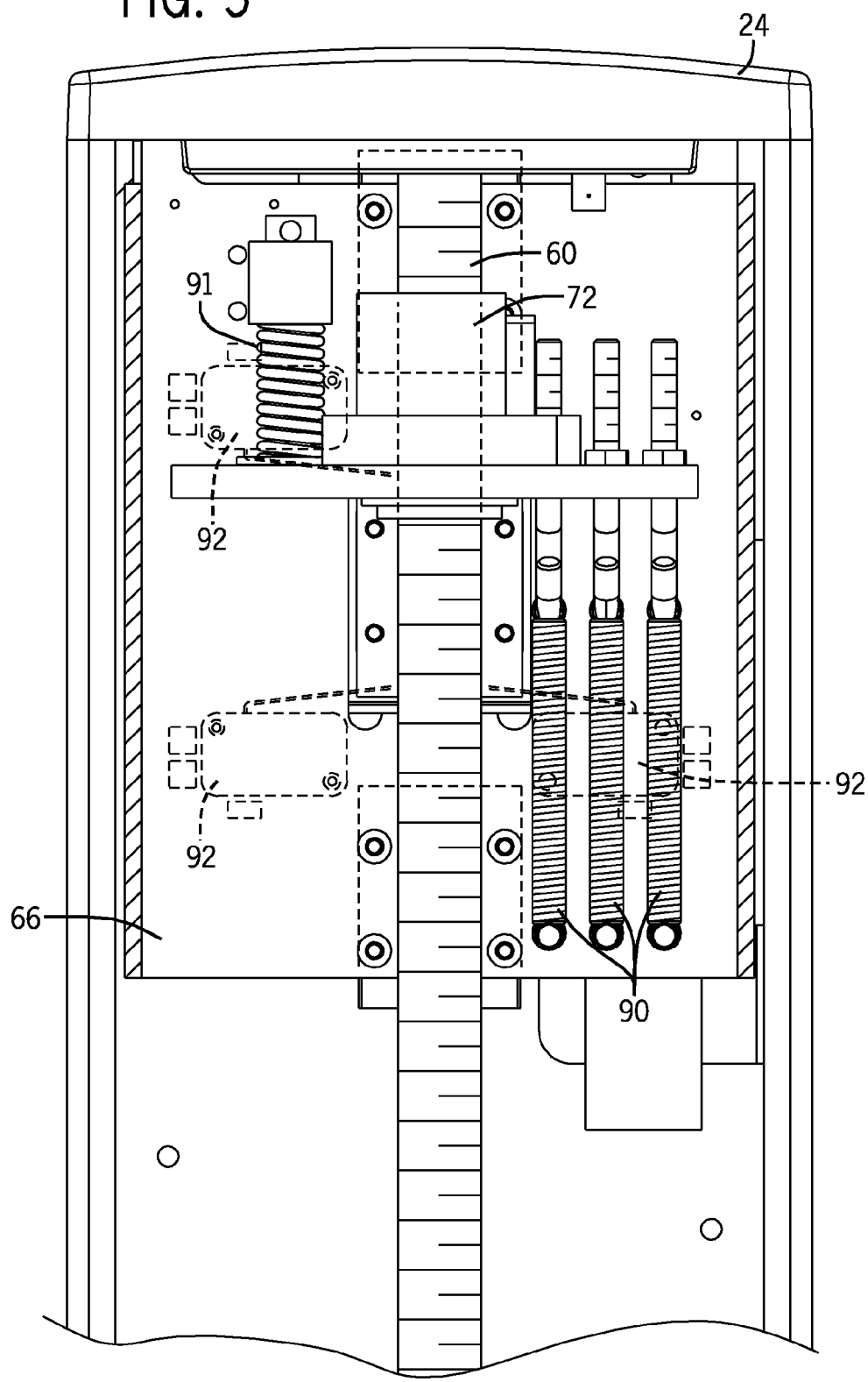
FIG. 5 is a view taken along line 5-5 in FIG. 4.

As best shown in FIG. 5, it may be desirable to connect vibration dampening springs 90 to the cross plates 66 to which the follower 72 is mounted, although the dampening springs 90 may not be necessary. In any event, the system 10 also includes trip switches 92 and spring 91 which are used to limit the amount of vertical force that can be applied by the Z-axis vertical screw drive. FIG. 5 shows only one spring 91 on one side of the lead screw 60, but it may be preferred to include another spring 91 on the other side of lead screw 60 in order to balance the load when limiting the amount of vertical force that can be applied by the Z-axis vertical screw drive. In general, if the force exerted by the Z-axis drive exceeds the threshold spring force for spring 91 (or pair of springs 91), the distance between the upper and lower trip switches 92 will not coordinate and the control system will disable further Z-axis motion in the desired direction. Motion will, however, preferably be allowed in the reverse direction.

With hand-held pipettors, pipette tips 14 are typically attached by forcing the tip onto a tip fitting, which is a rapid and convenient way or users to install a new clean pipette tip. It is not unusual for the user to apply approximately 1 lb. of force to attach a single tip. With a manually-directed, multi-channel electronic pipetting system 10 constructed in accordance with the invention, 96-pipette tips must attached contemporaneously. If the same tip attachment technique is used, then the minimum force that the pipettor must apply is multiplied by 96, and in reality the actual force is frequently higher. When attaching multiple tips simultaneously, some tips will fully attach or bottom out before others, and once bottomed out more force is required to move downward. This problem can be aggravated by the tendency of the rack 34 holding the tips 14 to bow when large attachment forces are applied. As a result, an extra margin of force is required to ensure that all tips are correctly attached. Assuming that each tip 14 requires at least 1 lb. of attachment force, the total force must therefore be approximately 150 to 200 lbs. for a tip rack 34 of 96 tips.

Figure 16:
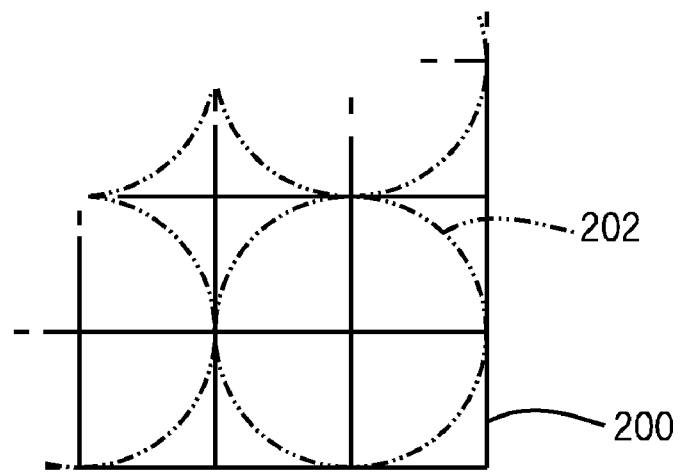
FIG. 16 is a schematic drawing illustrating the relative size and location of wells in a 96-well plate compared to wells in a 384-well plate.

While the vertical drive mechanism must be able to provide sufficient attachment force, it is undesirable to allow the vertical drive mechanism to exert excessive force under normal operating conditions when not attaching tips. For example, refer to FIG. 16, which schematically illustrates the relative positions between a well in a 384-well plate 200 and a well in a 96-well plate 202 (show in phantom). If the pipette tips 14 are aligned with the center of the wells in a 96-well plate, but a 384-well plate is located on the nesting receptacle below the pipetting head, the tips will crash on the well walls in the 384-well plate when the user lowers the pipetting head into the wells to aspirate liquid from the wells. It is desirable to limit the available downward force under normal operating conditions in part to limit the amount of potential damage that can occur with such misalignment. In addition, if high forces are applied during normal operations, a user could be injured if their hand was caught under the pipette tips. Therefore, in accordance with one aspect of the invention, a force limiting mechanism is built into the Z-axis vertical drive mechanism to limit the amount of force that the pipetting head 12 can exert under normal use.

Figure 7:
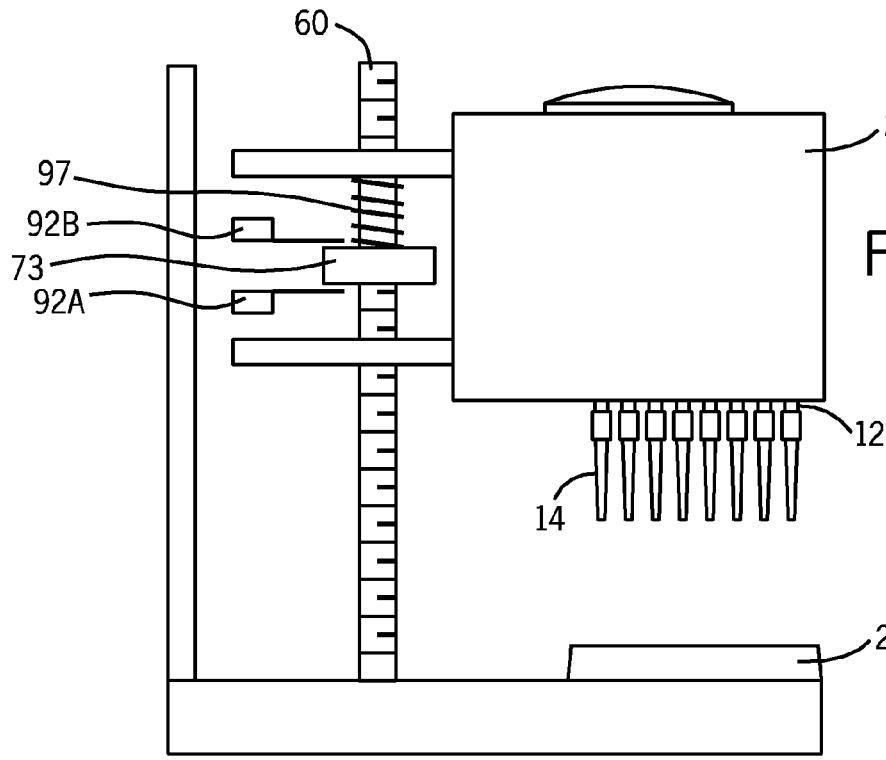
FIG. 7 is a schematic drawing illustrating a force detector for the vertical drive mechanism to stop vertical motion when the detected force exceeds a maximum threshold value.
Figure 8:
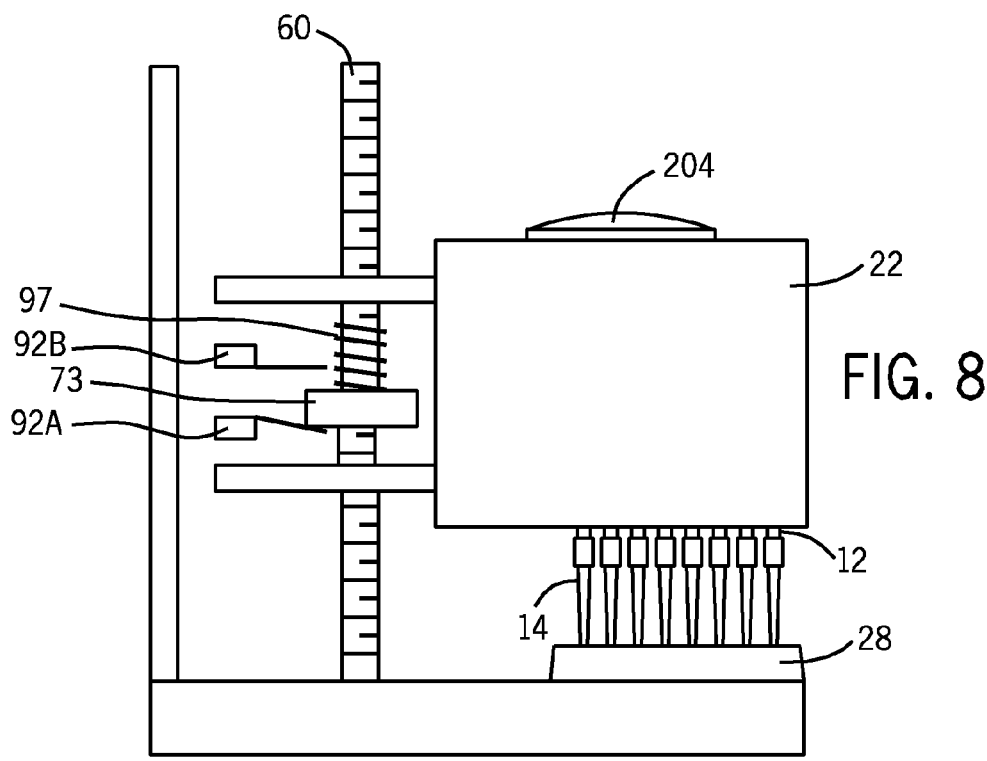
FIG. 8 is a schematic view similar to FIG. 7 illustrating the pipette tips in a crash condition.
Figure 9:
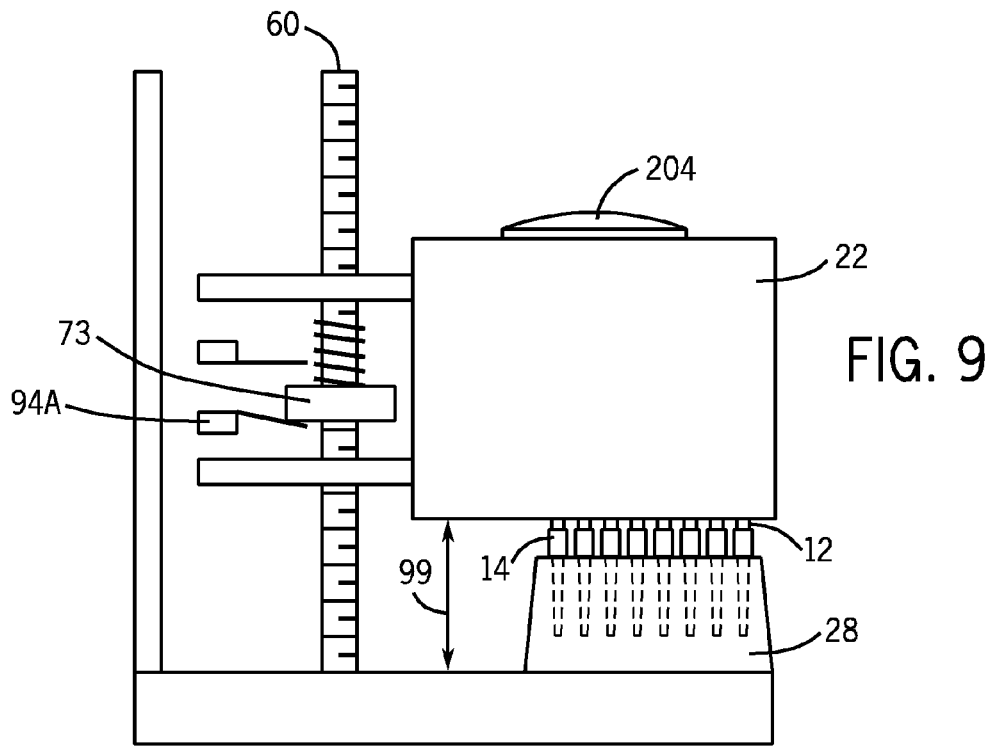
FIG. 9 is a schematic view similar to FIGS. 7 and 8 illustrating an override procedure for tip attachment even though the force detector has detected a force exceeding the threshold value.

Referring now to FIGS. 7-9, in normal operating, the lead screw 60 drives the carriage 22 and pipettor head 12 up or down using a spring supported lifting nut 73. The force from the lifting nut 73 is transferred to the carriage 22 and pipettor head 12 through a spring 97 that normally remains in a neutral position when carrying the weight of the pipettor head 12, see FIG. 7.

If the user drives the pipettor head 12 down onto an object (for example a wellplate that is not aligned), then one of the two safety switches 92A, 92B will be activated, see FIG. 8. In this condition, the vertical motor will stop further downward movement, preventing damage to the object under the tips. However, upward movement is still allowed, so the user can lift the pipetting head 12 off of the object it collided with. The upper safety switch 92B works in an identical fashion, preventing further upward movement if the carriage 22 is moved up into an obstacle such as the underside of a cabinet or fume hood in the lab.

This mechanical switch successfully limits the vertical force applied by the pipettor head 12 during normal operation. However, without additional techniques, the switch mechanism prevents the user from applying enough force to successfully attach tips.

Referring to FIG. 9, as the user moves the pipette head 12 down onto the tip box 34, the lower safety switch 92A will trip when the tip fittings on the pipetting head 12 engage the pipette tips 14 in the tip box 34. The software detects the switch tripped and stops further downward movement. However, it also looks at the position feedback encoder 158 for the vertical drive and determines whether the vertical position is unique to the tip box 34. More specifically, when the pipetting head 12 is mounted in the carriage 22 sensors determine the size and type of pipette tips that are used in connection with the mounted pipetting head, and in particular identifies the correct height 99 (arrow 99 in FIG. 9) for the pipette tips 14 in the tip box 34. The software confirms whether the switch was tripped at a height corresponding to the correct height 99 for the pipette tips 14 in the tip box 34. It also confirms that the horizontal position is aligned with a tip rack 34 being located in one of the nesting receptacles 18, 20 on the deck 16. If all of these conditions are true, then the software illuminates a button 204 on the top of the carriage 22, or provides another signal, to let the user know that the system 10 is ready to attach tips.

The user must now push down on the control handle 30 and also push button 204 on top of the carriage 22 to start the tip attachment cycle. In accordance with the invention, it is not necessary that the tip attachment button 204 be located on top of the carriage 22. The tip attachment button 204 may be located at another location on the system 10, or may be located in a separate location such as on the laboratory bench top. Once the tip attachment cycle is initiated, system 10 processes a series of steps to attach tips: 1) the normal hand controller 30 servo control through the load cell 32 is disconnected; 2) the horizontal motor drive is disabled to prevent the head from moving left or right; 3) the vertical lead screw 60 drives the carriage 22 and pipetting head 12 down a predefined distance; 4) the vertical movement is stopped for about 250 ms to allow the tips to fully attach; 5) the vertical lead screw 60 is driven up to clear the tip rack 34; 6) the normal hand controller servo control through the load cell 32 is restored.

In another aspect of the invention, it has been found to be important to protect against unintended motion during system faults. As mentioned, both the vertical and the horizontal motors 74, 108 normally follow the user's hand motion through closed loop servo control (FIG. 6). Safe operation is ensured through a combination of user judgment (similar to any other power tool) and safety switches which shut down the vertical motion if a collision is detected. However, if a failure was to occur that interrupts the normal servo feedback loop, then the possibility exists for an un-commanded movement of the motors 74, 108. Several techniques have been developed to ensure that servo loop failures are detected and that the unit returns to a safe state when failure is detected.

For example, the loss of position feedback can result in un-commanded moves at maximum speed. Referring to FIG. 6, loss of position feedback from the encoder 156 is likely to cause the actual position counter 158 to freeze at its last value. As the target position counter 146 continues to advance, a large position error results in line 149 causing the PID filter 150 to command large corrective action from the motor 74, 108. Hence, a runaway condition exists. Various techniques can be used to ensure that such a runaway condition cannot develop. For example, motor current can be monitored, and the system can issue a fault condition when a substantial change in current occurs. Alternatively, the system can use a "checking" processor 206, see FIG. 10, which is responsible for monitoring the main servo control loop. This checking processor 206 is able to stop the respective motor 74, 108 at any time, and a failure of either the main control loop or the check processor results in the motor stopping.

Figure 10A:
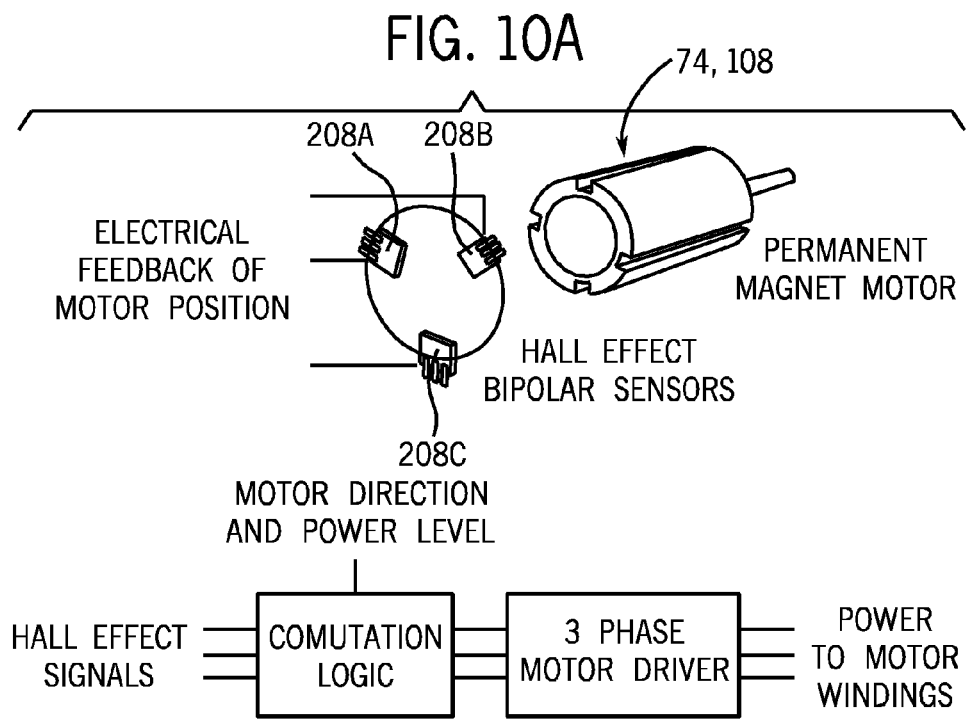
FIG. 10A is a schematic drawing illustrating Hall-effect sensors on the servo motors for the horizontal and vertical drive mechanisms.
Figure 10:
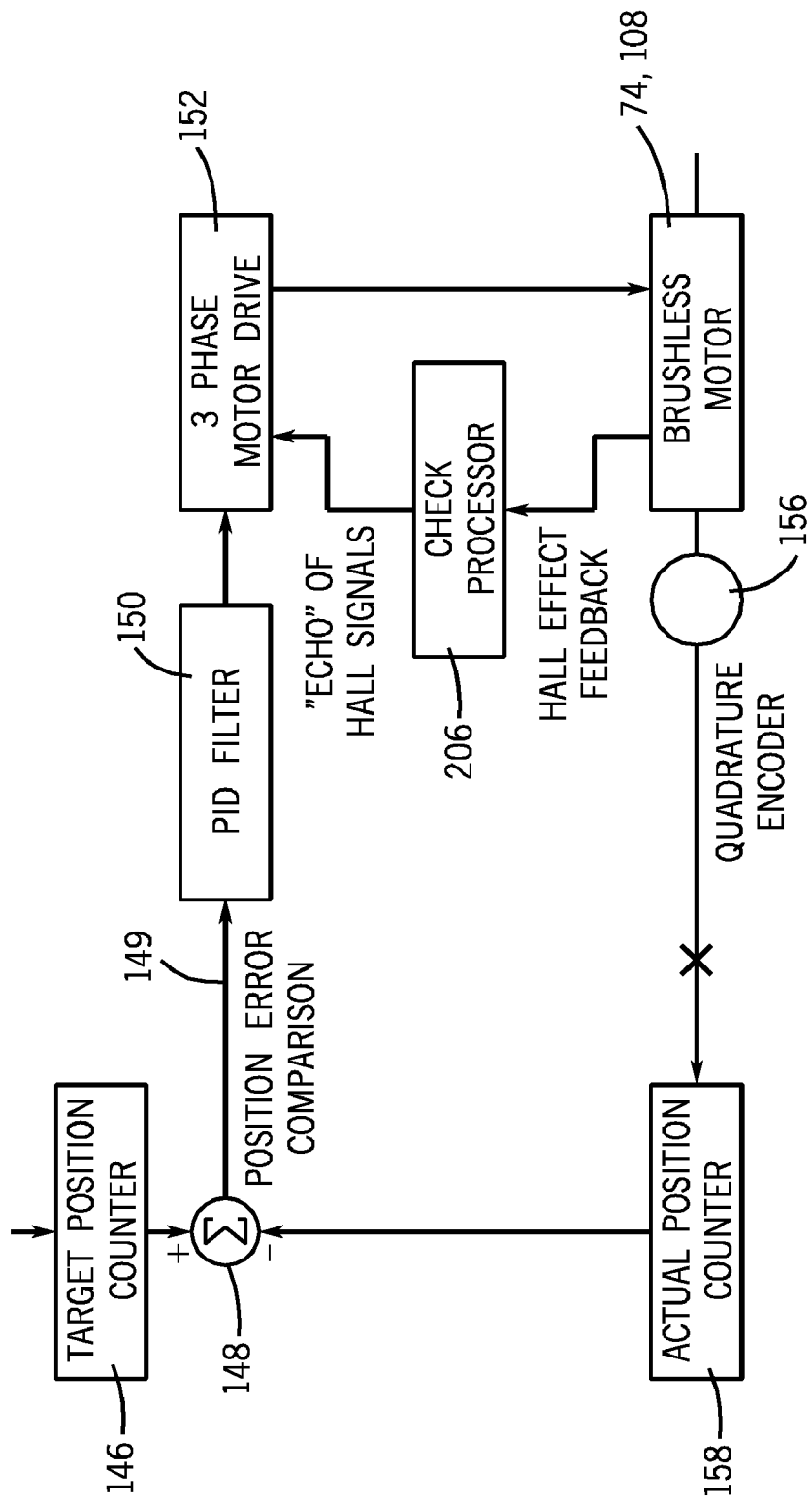
FIG. 10 is a block diagram illustrating the use of a check processor within the control loop described in FIG. 6 in order to stop a drive motor in case of a fault condition.

Motor halting can be accomplished through Hall-effect interruption. Referring to FIG. 10A, the brushless servo motors 74, 108 each contain a three-phase winding and three Hall-effect sensors 208A, 208B, 208C. The three Hall-effect sensors 208A, 208B, 208C provide an electrical indication of the rotor position that changes every 30 degrees of rotation. The signals from the three signal Hall-effect sensors 208A, 208B, 208C are used to determine which combination of the three windings of the motor 74, 108 should be energized to achieve either clockwise or counterclockwise rotation. The polarity of the voltages applied to the motor windings is continuously updated as the motor turns. If the voltages on the windings are not updated, the motor 74, 108 will come to an abrupt halt within 60 degrees of rotation. Although it is normally possible to run a three phase motor without Hall-effect position feedback, in the preferred embodiment of the invention, the Hall-effect sensors are the only device capable of providing the correct winding sequences and therefore are essential to the motor turning. If the Hall-effect signals are interrupted, the motor will stop or hold its last position. In either case, the motor will not travel far enough to runaway. This characteristic is used to advantage as an infallible technique for stopping the motors in the event of a detectable error. Referring to FIG. 10, signals from the three Hall-effect sensors 208A, 208B, 208C from the motor 74, 108 are sent to the check processor 206 and echoed out of three separate pins of the check processor 206. This echo is performed continuously until an error condition is detected. In FIG. 10, the "x" in the line from the encoder 156 indicates the presence of an error condition.

Figure 11:
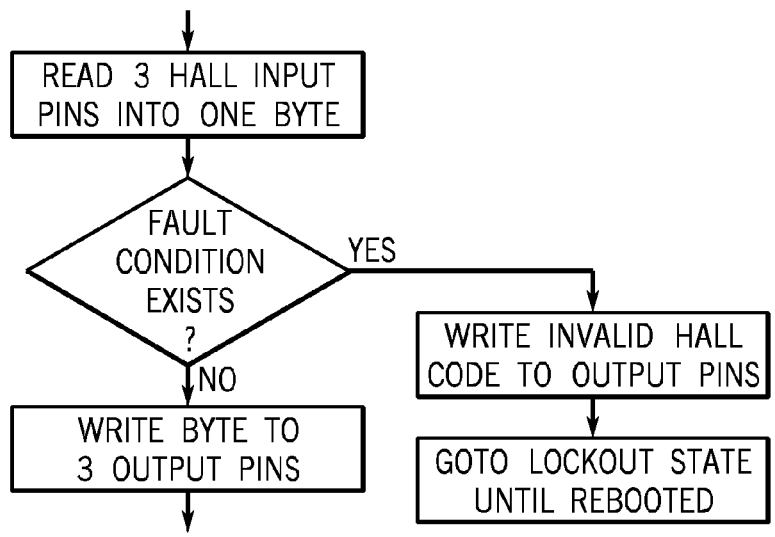
FIG. 11 is a logical flow diagram illustrating an echoing feature of the check processor.

FIG. 11 is a logic diagram illustrating the echoing logic in the check processor 206. Essentially, the check processor 206 reads three Hall-effect sensor input pins, and determines whether a fault condition exists. If no fault condition exists, the check processor 206 writes the byte to three output pins to echo the signal to the three-phase motor drive 152. On the other hand, if a fault condition exists, the check processor 206 writes an invalid Hall-effect code (000 or 111) to the pins and stops echoing the inputs. Failure to transmit a proper echoed signal causes the motor 74, 108 to stop as the three-phase motor driver is unable to provide the correct commutation sequence.

In the event that the check processor 206 fails, it is reasonable to expect that the echoed outputs will either freeze at their last state or go to an invalid state. In either case, if a detected fault condition or a check processor 206 failure, the motor will not run correctly. This is a robust technique for stopping the motor 74, 108 in a fail safe manner.

Figure 13:
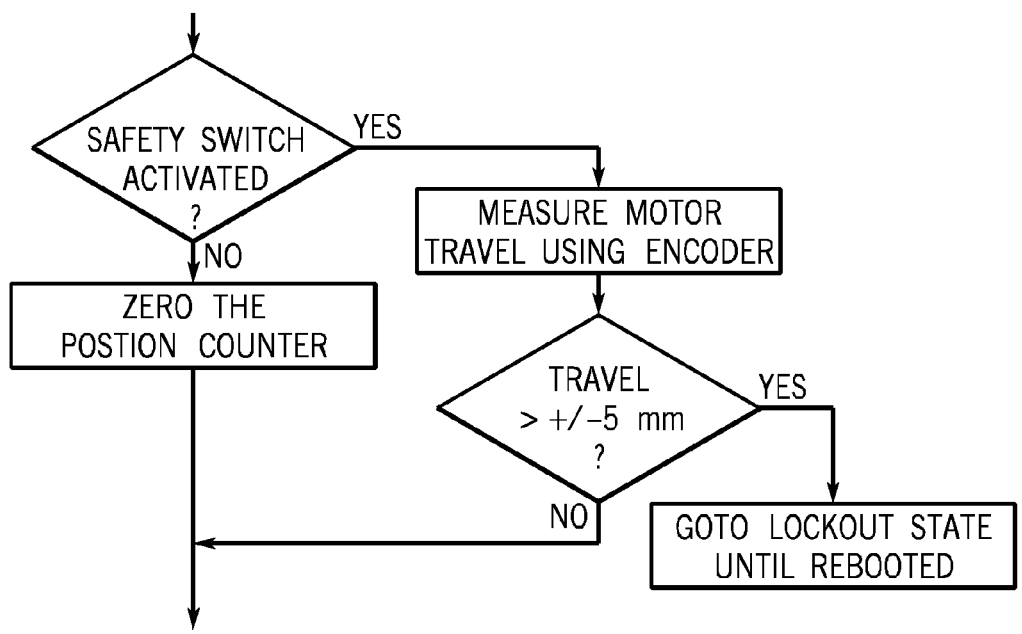
FIG. 13 is a flow diagram illustrating the logic within the check processor pertaining to the redundant safety switch.
Figure 12:
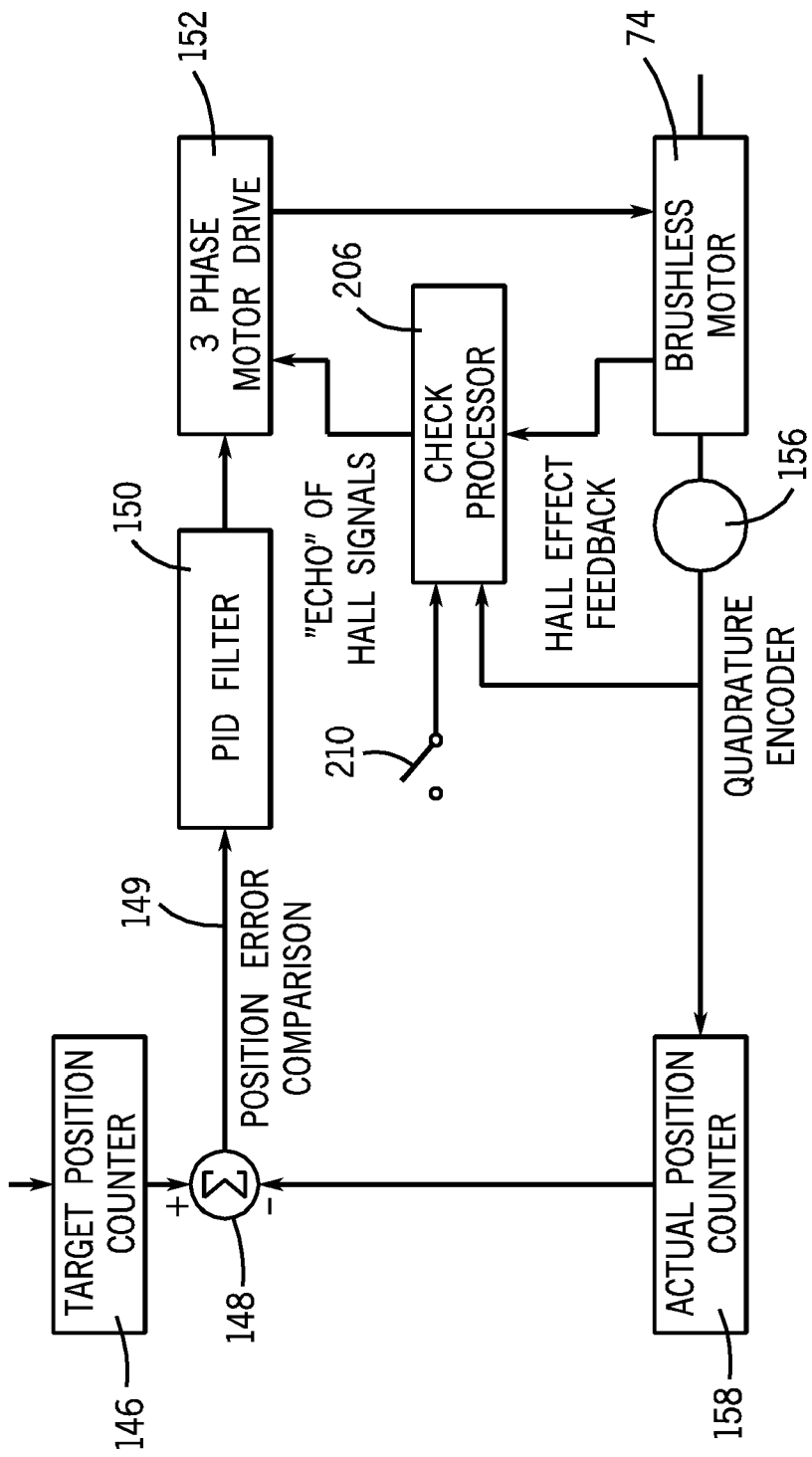
FIG. 12 is a block diagram illustrating the use of a redundant safety switch.

Of course, the check processor needs to be capable of detecting various types of faults. FIGS. 12 and 13 pertain to the use of a duplicate safety switch 210 for vertical mechanical crashes. As described earlier, mechanical crashes are detected by a spring loaded safety switch that signals the main processor that a collision has occurred. However, in accordance with the preferred embodiment of the invention, a second mechanically redundant switch 210, FIG. 12, is connected to the check processor 206. Physically the safety switch 210 is redundant with switch 92A (FIGS. 7-9), but switch 210 is connected to the check processor 206.

FIG. 13 describes the logic in the check processor 206 pertaining to the input from the redundant safety switch 210, FIG. 12. If the safety switch 210 is not activated, the position counter within the check processor 206 is zero. However, if the redundant safety switch 210 is tripped, indicating that a crash condition has been encountered, the check processor will measure the continued travel of the motor by counting the encoder 156 output, see FIG. 12 which shows the output signal from the encoder 156 being fed to the check processor 206. When the redundant switch 210 is tripped, the check processor 206 starts to monitor the movement of the motor 74 through the encoder feedback. A small amount of additional movement is allowed (corresponding to approximately 5 mm), to give the motor time to decelerate and to compensate for slight differences in the timing of the two switches. Therefore, even if the safety switch 92A or the control system has failed and there is tip crash, the check processor 206 will prevent unintended motion beyond ±5 mm. In other words, after the redundant switch 210 is tripped and +/−5 mm of travel occurs, it is considered a fault condition and the check processor 206 goes to a lockout state.

Figure 14:
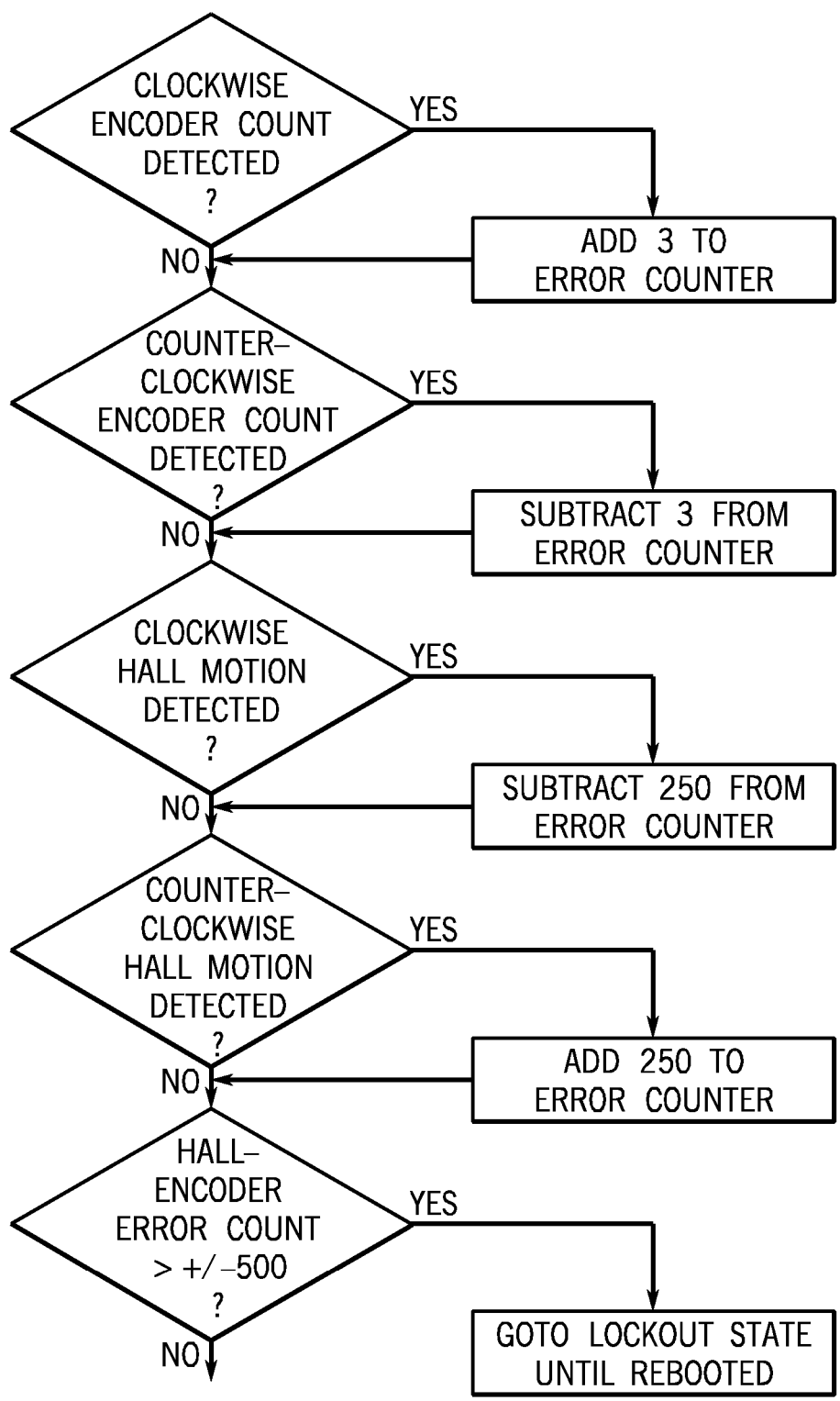
FIG. 14 is a flow diagram illustrating a counting protocol within the check processor to ensure proper operation of the servo motor encoder.

FIG. 14 illustrates another use of the check processor 206, which is to check the accuracy of the output from the encoder 156. As discussed, the brushless servo motors 74, 108 used for both vertical and horizontal motion each contain a three-phase winding and three Hall-effect sensors and each also contain an encoder 156 for position feedback. The encoder 156 outputs a relatively large number of pulses per motor revolution (1000 for the vertical motor) whereas the Hall-effect sensors change state only 12 times per revolution. However, the signals from the Hall-effect sensors can be used as a validation check to detect complete or partial failures of the encoder 156.

For every Hall-effect change of state, there are 83.33 encoder pulses (1000/12). A counter is used within the check processor 206 that is based on the lowest common denominator between the two. This is 3000 counts per revolution since 3000/1000=3 and 3000/12=250. FIG. 14 illustrates the operation of the counter in the check processor 206. Referring to FIG. 14, each motion of the encoder 156 should be balanced by a change in the Hall-effect sensor position. If an error between the two accumulates greater than two Hall-effect sensor changes, then this is considered a fault condition and the check processor 206 goes to a lockout state.

Figure 15:
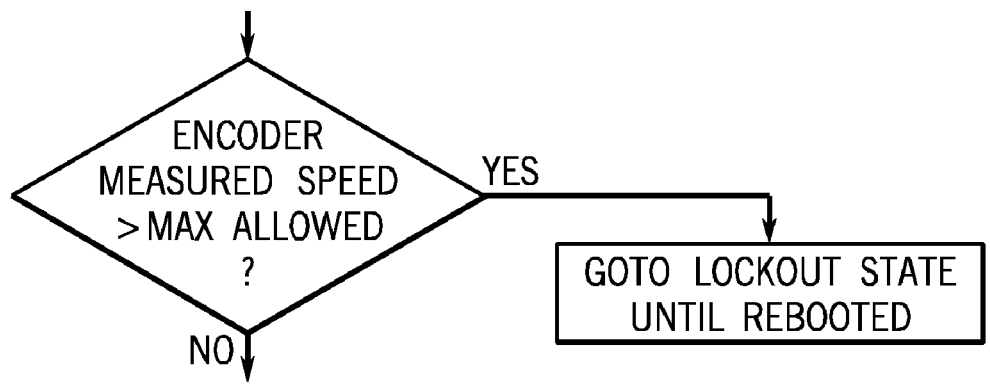
FIG. 15 is a flow diagram illustrating protocol within the check processor to ensure that the speed of either the vertical drive or the horizontal drive does not exceed a maximum speed limit.

Referring now to FIG. 15, the check processor 206 is also used to detect a motor overspeed condition. When normal motions are being executed, the user is responsible for the speed of the actual motion. However, an upper limit is imposed on the speed throughout the range of travel by the position dependent speed limiter 142 as described earlier. In connection with FIG. 6, conditions such as an undetected software bug could potentially result in un-commanded motion at high speed, even though the encoder feedback is operating correctly. This condition can be detected in the check processor 206 by looking for speeds beyond a maximum speed and stopping the motor if they occur, see FIG. 15. The speed can be reliably measured from the encoder 156, by counting the number of encoder pulses over a period of time, say 100 ms. If the encoder pulse count exceeds a predetermined limit, the motor will be stopped.

In the foregoing description, certain terms have been used for brevity, clearness, and understanding. No unnecessary limitations are to be inferred therefrom beyond the requirement of the prior art because such terms are used for descriptive purposes and are intended to be broadly construed. The different configurations, systems, and method steps described herein may be used alone or in combination with other configurations, systems and method steps. It is to be expected that various equivalents, alternatives and modifications are possible within the scope of the appended claims.

What is claimed is:

1. An electronic multi-channel pipetting system comprising:
 a pipetting head carriage;
 a multi-channel pipetting head carried in the carriage, the multi-channel pipetting head having a plurality of pipette tip fittings arranged in a two-dimensional array of rows and columns;
 a pipetting motor that drives the multi-channel pipetting head to aspirate and dispense;
 a deck adapted to hold at least one multi well-plate, reagent reservoir or tip rack;
 a motorized drive mechanism having at least one motor moving the pipetting head with respect to the deck, the drive mechanism including at least a vertical drive mechanism having a vertical drive motor for moving the pipetting head vertically with respect to the deck with sufficient force to mount pipette tips to each of the pipette tip fittings in the multi-channel pipetting head;
 a control handle and a motion control system configured such that the multi-channel pipetting head moves with respect to the deck via the drive mechanism in response to force applied to the control handle by an operator; and
 a detector for the vertical drive mechanism that provides a safety signal to the motion control system if an unintended obstacle is met and when the operator applies force on the control handle to move the pipetting head carriage and multi-channel pipetting head downward, wherein the motion control system stops the vertical drive motor for the vertical drive mechanism in response to the safety signal.

2. The electronic multi-channel pipetting system as recited in claim 1 wherein the control handle is mounted on the pipetting head carriage.

3. The electronic multi-channel pipetting system as recited in claim 1 further comprising a tip attach button that must be activated in order to lower the pipetting head with sufficient force to attach pipette tips to the plurality of tip fittings on the pipetting head.

4. The electronic multi-channel pipetting system as recited in claim 3 wherein the tip attach button is located on the pipetting head carriage.

5. The electronic multi-channel pipetting system as recited in claim 1 wherein the deck has at least one wellplate nesting receptacle.

6. The electronic multi-channel pipetting system as recited in claim 1 further comprising an upstanding tower and further wherein the pipetting head carriage is mounted to the tower.

7. The electronic multi-channel pipetting system as recited in claim 1 wherein the drive mechanism further includes a horizontal drive mechanism having a horizontal drive motor for moving the pipetting head horizontally with respect to the deck; and further wherein the multi-channel pipetting head moves either horizontally, vertically or both with respect to the deck in response to the direction of force applied by the operator on the control handle.

8. The electronic multi-channel pipetting system as recited in claim 1 wherein the array of pipette tip fittings includes at least 96 pipette fittings.

* * * * *